United States Patent
Grech

(10) Patent No.: US 8,092,569 B2
(45) Date of Patent: Jan. 10, 2012

(54) METHODS OF GENERATING PHOSPHORUS FERTILIZERS THROUGH THE UTILIZATION OF MICROBIAL FERMENTATION TECHNOLOGY

(75) Inventor: Nigel Grech, Fresno, CA (US)

(73) Assignee: Sci Protek, Inc., Visalia, CA (US)

( * ) Notice: Subject to any disclaimer, the term of this patent is extended or adjusted under 35 U.S.C. 154(b) by 314 days.

(21) Appl. No.: 11/982,574

(22) Filed: Nov. 2, 2007

(65) Prior Publication Data

US 2008/0105018 A1  May 8, 2008

Related U.S. Application Data

(60) Provisional application No. 60/857,470, filed on Nov. 6, 2006.

(51) Int. Cl.
  *C05F 11/08* (2006.01)
  *C01B 25/163* (2006.01)

(52) U.S. Cl. .............................. 71/10; 423/304; 423/305

(58) Field of Classification Search .................. 423/304, 423/305; 71/10
See application file for complete search history.

(56) References Cited

U.S. PATENT DOCUMENTS

| | | | |
|---|---|---|---|
| 3,102,804 A * | 9/1963 | Engelhart | 71/10 |
| 3,930,799 A | 1/1976 | Eweson | |
| 4,100,023 A | 7/1978 | McDonald | |
| 4,162,153 A | 7/1979 | Spector | |
| 4,169,048 A | 9/1979 | Albers, Sr. | |
| 4,221,571 A | 9/1980 | Rhoades | |
| 4,252,901 A | 2/1981 | Fisher et al. | |
| 4,311,510 A | 1/1982 | Graefe | |
| 4,486,216 A * | 12/1984 | von Raven et al. | 71/8 |
| 5,178,776 A | 1/1993 | Graziano et al. | |
| 5,656,059 A | 8/1997 | Monster et al. | |
| 5,810,903 A | 9/1998 | Branconnier et al. | |
| 5,866,003 A | 2/1999 | Okubo et al. | |
| 6,254,654 B1 | 7/2001 | Van Barneveld | |
| 6,420,167 B1 | 7/2002 | Okamoto et al. | |
| 6,423,531 B1 | 7/2002 | Hince et al. | |
| 6,692,642 B2 | 2/2004 | Josse et al. | |
| 6,699,707 B1 | 3/2004 | Hince et al. | |
| 7,179,642 B2 * | 2/2007 | Dvorak | 210/612 |
| 7,211,429 B1 * | 5/2007 | Rudas | 435/262 |
| 2001/0055239 A1 | 12/2001 | Rhee | |
| 2004/0000179 A1 * | 1/2004 | Hiraki | 71/10 |
| 2004/0025715 A1 | 2/2004 | Bonde et al. | |
| 2004/0182780 A1 | 9/2004 | Lee | |
| 2005/0044911 A1 | 3/2005 | Shimose | |
| 2006/0222585 A1 | 10/2006 | Verser et al. | |
| 2007/0062233 A1 | 3/2007 | Burnham | |
| 2007/0169526 A1 | 7/2007 | Van Der Weide | |

FOREIGN PATENT DOCUMENTS

| | | |
|---|---|---|
| AT | 197287 T | 11/2000 |
| AU | 4764993 A | 3/1995 |
| DE | 69329622 D1 | 12/2000 |
| DE | 69329622 T2 | 6/2001 |
| DE | 69711105 D1 | 4/2002 |
| DE | 69711105 T2 | 8/2002 |
| EP | 0670821 A1 | 9/1995 |
| EP | 0801033 A | 10/1997 |
| EP | 0801033 A2 | 10/1997 |
| JP | 9327686 A | 12/1997 |
| JP | 3420460 B2 | 6/2003 |
| JP | 34320460 B2 | 6/2003 |
| WO | 9506623 A | 3/1995 |
| WO | 2006046948 A | 5/2006 |

OTHER PUBLICATIONS

Xiali Guo et al, "Anaerobic conversion of phosphate by the mixed inoculum", Zhejiang Daxue Xuebao, Nongye Yu Shengming Kexueban (2005), 31 (1), 88-91. (Abstract only).*
H.G. Schlegel: "General Microbiology" 1986, Cambridge university Press, Cambridge, XP002489663 p. 84-87, p. 99, p. 306-309.
Rutishauser et al. Phosphine Formation from Sewage Sludge Cultures. Anaerobe. Oct. 1999, vol. 5 No. 5 pp. 525-531, especially p. 525, col. 1 & 2; p. 526, col. 1; p. 530, col. 1 & 2 & table 2.
Roels et al. Biological formation of volatile phosphorus compounds Bioresoource Technology Sep. 1, 2001 vol. 79 No. 3 pp. 243-250, especially p. 243, col. 1 & p. 244, col. 1.
Han El Al. Phosphine & methane geeneration by the addition of organic compounds containing corbon/phosphorus bonds into incubated soil. Chemosphere. Nov. 2002, vol. 49 No. 6 pp. 651-657.
Jenkins et al. Phosphine generation by mixed & monoseptic cultures of anaerobic bacteria. The Science of the Total Environment. Apr. 2000, vol. 250 No. 1 pp. 73-81 especially p. 74, col. 1—p. 75, col. 1 & p. 77, col. 2—p. 78, col. 1 & table 2 & p. 80, col. 1.
PCT/US2007/023200—IPEA.
PCT/US2007/023200—ISR.
PCT/US2007/023200—IPR.
Sodium Phosphate Listing Background Document for the Inorganic Chemical Listing Determination (2002).

* cited by examiner

*Primary Examiner* — Wayne Langel
(74) *Attorney, Agent, or Firm* — Mark D. Miller

(57) ABSTRACT

This invention includes uses and methods of preparing phosphites and/or hypophosphites (and their polymeric forms and/or their salts) and phosphite-based agrochemicals (fertilizers and biocides) from phosphate or other naturally occurring or synthetic phosphorus sources using anaerobic microbial fermentation. The fermentation process produces both a liquid and solid phase phosphite/hypophosphite salts which can be used as an agrochemical product.

35 Claims, No Drawings

METHODS OF GENERATING PHOSPHORUS FERTILIZERS THROUGH THE UTILIZATION OF MICROBIAL FERMENTATION TECHNOLOGY

This application claims the benefit of U.S. provisional application Ser. No. 60/857,470 filed on Nov. 6, 2006, which is incorporated herein by this reference.

BACKGROUND OF THE INVENTION

1. Field of the Invention

The present invention relates to generating phosphorus (P) fertilizers using microbial fermentation technology, and more particularly by converting phosphate sources to more chemically reduced forms of phosphorus by anaerobic microbial fermentation, with the end products being suitable for use in agriculture.

2. Description of the Prior Art

Phosphites (also known as phosphonates) are a natural component of the phosphorus cycle in soil, plant and marine plant systems. They are defined as the salts of phosphorous acid ($H_3PO_3$). Hypophosphites are the salts of hypophosphorous acid. In the following description of this invention, the term phosphite will sometimes be used to describe these salts of phosphorous/hypophosphorous acid. In modern agriculture the phosphorus cycle can be severely disrupted by the widespread use of biocides and inorganic fertilizers. These factors often result in phosphorus limitations in many agricultural soils. In addition, it is known that phosphate based fertilization is not very efficient in many soils due to fixation and adsorption. Moreover, foliar absorption of phosphate is also very poor or non-existent.

Phosphites have been known for some time to have activity in both plants and microbes as sources of plant nutrients (Lovatt, U.S. Pat. No. 5,514,200) and as biocidal agents (Thizy, U.S. Pat. No. 4,075,324) and are now well established in terms of their agrochemical usage. It has also been determined that phosphite-based phosphorus fertilizers demonstrate superior penetrating abilities across plant foliage, and have a propensity to remain more available in the soil and not become as fixed or adsorbed—as is the case with phosphate. Phosphite-based fertilizers are also far more efficient at delivering phosphorus than phosphate-based fertilizers due to having one less oxygen molecule, and as such the proportion of "P" in the molecule is correspondingly higher. Phosphites are also much more soluble and less prone to precipitation and soil adsorption. The superior solubility of phosphites is also advantageous in terms of the anion in the salt. Greater solubility of ammoniacal, potassium, magnesium and calcium salts result in more efficient nutritional delivery whether applied to the soil or particularly to the plant foliage than the corresponding phosphate salt(s).

Phosphites have also been shown to exhibit marked activity against certain microbes such as fungi and bacteria and are used as biocides.

Currently the manufacture of phosphorus fertilizers mainly consist of manufacturing the acid and then reacting the acid with certain bases in order to generate a fertilizer salt such as ammonium phosphate, potassium phosphate, potassium phosphite, etc. These methods generally involve highly reactive and generally exothermic reactions. Also many of the reactants are chemically hazardous. Commercially most phosphites are mainly produced through the reaction of phosphorus trichloride and water, a very hazardous and dangerous reaction. Phosphorous acid is extracted from the products of the reaction and purified. It is an expensive and hazardous process. It would therefore be very beneficial if a less hazardous and more efficient process could be found that could produce phosphites/hypophosphites.

Anaerobic microbes are abundant in nature and mediate many complex biochemical reactions in nature. Any environment where oxygen is absent or limiting, anaerobic metabolism can take place. Examples of anaerobiosis can be found in ecosystems such as in marshes and stagnant water bodies where organic matter decomposes in the absence of oxygen and leads to the on formation of 'marsh gas'. Marsh gas is largely methane. Anaerobic putrefication and degradation of organic matter is usually accompanied by unpleasant odors of hydrogen sulfide and of organic compounds that contain sulfur, such as mercaptans (any sulfur-containing organic compound). In such reducing conditions, oxygen rich molecules are not abundant.

SUMMARY OF THE INVENTION

This invention describes uses and methods of preparing phosphites and/or hyposphosphites (and their polymeric forms and/or their salts) and phosphite-based agrochemicals (fertilizers and biocides) from phosphate or other naturally occurring or synthetic phosphorus sources using anaerobic microbial fermentation. The fermentation process will produce both a liquid and solid phase phosphite/hypophosphite salts which can be used as an agrochemical product. After removal from the fermentation vessel, the liquid phase is filtered and packaged. For application to plants the liquid material is further diluted with water and applied to plants. The solid phase material in the reaction chamber is removed, dried and can then be used as a solid fertilizer either applied as is, blended with other solids (such as fertilizers and clays) or diluted in water and applied to plants. The derived phosphite/hypophosphite-based fertilizers are stable and may be mixed into solutions having a pH that is acceptable to plant foliage, and into other solutions having a root-acceptable pH. When extracted from the fermentation vessel, the material can be dried or further diluted with water, or made into a suspension.

It is therefore an object of the present invention to provide processes by which naturally occurring soils are used to generate phosphites and/or hypophosphites from phosphates or other naturally occurring or synthetic phosphorus sources by anaerobic fermentation.

It is also an object of the present invention to provide processes by which naturally occurring microorganisms are used to generate phosphites and/or hypophosphites from phosphates or other naturally occurring or synthetic phosphorus sources by anaerobic fermentation.

It is also an object of the present invention to provide processes by which naturally occurring soils and microorganisms are used to generate phosphites and/or hypophosphites from phosphates or other naturally occurring or synthetic phosphorus sources by anaerobic fermentation; in some cases the soils provide a source of the microorganisms utilized to in the anaerobic fermentation process.

It is another object of the present invention to provide processes in which the phosphites and/or hypophosphites that are generated by anaerobic fermentation are used to formulate agrochemicals such as fertilizers, biocides and other agrochemicals, for use in horticulture and elsewhere.

It is another object of the present invention to use anaerobic bacteria in the fermentation process to produce phosphites and/or hypophosphites from phosphates or other naturally occurring or synthetic phosphorus sources.

It is another object of the present invention to use anaerobic fungi in the fermentation process to produce phosphites and/or hypophosphites from phosphates or other naturally occurring or synthetic phosphorus sources.

It is another object of the present invention to provide processes in which the phosphites and/or hypophosphites that are generated by anaerobic fermentation are applied to plants, micro-organisms or the soil.

Methods of Generation

The following ingredients are mixed together into a slurry and placed in an air tight vented container: a suitable phosphate source, an anaerobic soil sample (containing anaerobic microbes and essential nutrients), or a sterile soil to which a pure culture of selected microbes are added, a carbon source, and water. Helium, Noble gases or nitrogen may be used to purge the air from the fermentation vessel. The air tight container has a one way vent to allow exhaust gases to be released and ensure minimal pressure build up in the fermentation vessel. Such a mixed microbial consortium capable of reducing phosphate may be obtained from locations in which soil has been cultivated anaerobically for several years. Such soils are preferred because the lack of aerobic conditions will favor the emergence of anaerobic microorganisms that proliferate under these low oxygen conditions. In anaerobic conditions, the energetic demands of microbial growth are not supplied by oxygen dependent respiration but rather by various redox reactions. Such reactions generate a reducing environment where highly oxidized materials (such as oxyanions) may be reduced to lower oxidation states. Such examples include, without limitation, sulfate to sulfides, chlorates to chlorides, phosphate to phosphite, nitrates to nitrides (and ultimately methane), etc. Hence it has been discovered that if a sufficiently low oxygen environment is provided, phosphate can be converted to lower oxidation states such as to phosphite (+III) and hypophosphite (+I). The result of the anaerobic fermentation process is the generation of reduced oxyacid salts of phosphorus such as phosphite and hypophosphite salts in the liquid and solid phase.

This invention describes methods to generate phosphites/hypophosphites for agrichemical, agricultural, horticultural and other uses. The compositions may be incubated for as little as a few days to as much as a few months. The reaction is accelerated by higher temperatures (10-40° C.). The result of the anaerobic fermentation process is the production of phosphites/hypophosphites which may then be used as is, further concentrated, diluted and/or mixed with other fertilizers and/or biocides to form compound fertilizers and/or other biocides and which may be in solid or liquid forms and used in agriculture/horticulture or elsewhere. Various microbial genera have been identified in this process such as, without limitation, *Clostridium, Vibrio, Klebsiella* and/or *Escherichia*. Generally it has been discovered that samples of populations of bacteria isolated from anaerobic soils have to a lesser or greater extent the ability to generate phosphites/hypophosphites from phosphate sources under anaerobic conditions. Samples of anaerobic soils have been collected from various locations in California and three such soils (designated rrs 12, rrs 15 & rrs 19), have shown promise generating phosphites from phosphates.

In the cultivation of the anaerobic microbes such as bacteria belonging to genera such as *Clostridium, Vibrio, Klebsiella* and/or *Escherichia* as well other anaerobes, it is desirable to employ growing conditions conducive to the proliferation of anaerobes. Various inductants include but are not limited to media additions such as those described by Long et al. in 1983 (Appl. Environ. Microbiol., 45: 1389-1393). Isolation of bacteria from the soil samples was undertaken and resulted in the identification of isolates capable of generating phosphite from phosphate.

The aforementioned invention can take the form of a static fermentation or a continuous fermentation system which provides environments favorable for anaerobic bacterial fermentation such that optimum digestion of the biomass and production of phosphites and their salts is maintained. In all cases helium, nitrogen or Noble gases may be used to purge the fermentation vessel.

In general, the biomass, preferably in the form of an aqueous slurry, is introduced into a fermentation reactor provided with an anaerobic environment. If the pH of the biomass slurry drops to about 4.8, the fermentation process may be impaired (i.e. the environment is too acidic to sustain effective anaerobic bacterial fermentation). Thus, a neutralizing agent can be added to the system to maintain a pH above about 4.8 in each reactor. Suitable neutralizing agents include ammonium, sodium, potassium and calcium salts of hydroxides, carbonates and bicarbonates. Preferably, calcium carbonate or calcium hydroxide is employed to maintain the desirable pH range of the system. The neutralizing agent can be added to the system at any point where it is needed to maintain the pH range. The base may be added alone or with the fresh biomass entering the fermentation process.

Examples of methods for generating the phosphites/hypophosphites are given below:

EXAMPLE 1

The following materials (generally the materials are in a fine state, initially ground to a particle size in the range of 10-40 mesh (ASTM), using well known comminution equipment, such as a Fitzpatrick mill were mixed together into a slurry and all the components except the soil were sterilized in an autoclave. The soil was added to the mixture and incubated at around 35° C. on an orbital shaker. Helium was initially fed into the fermentation chamber to purge the resident air. The daily results are set forth in the table below.

| Calcium Phosphate (colloidal) | 2 kg |
|---|---|
| Potassium Phosphate | 0.5 kg |
| Anaerobic soil (site rrs 15) | 300 g |
| Sucrose | 10 g |
| Sodium lactate | 1 g |
| $FeCl_2$ | 0.5 |
| $MnCl_2$ | 0.1 |
| ZnCl | 0.05 |
| CuCl | 0.02 |
| $S_e$ | 5 g |
| Solubor | 0.01 g |
| Water | 1.5 kg |

The initial pH of the mixture was adjusted to 7.5 with Hydrochloric acid. The mixture was agitated. Over the course of 20-30 days the pH of the media can drop to levels where fermentation is impaired, which may necessitate adjustment with a base such as calcium hydroxide.

Results: (Example 1)
Recovery of Phosphite and Hypophosphite (% w/w as a % of the total P)

| | Day 1 | 3 | 6 | 9 | 12 | 15 | 18 |
|---|---|---|---|---|---|---|---|
| PO3/HPO2 | 0 | 0 | 2 | 7 | 11 | 10 | 8 |

EXAMPLE 2

An inorganic phosphate source was used as in example 1. However, in this example a complex carbon source was used (wheat straw). No other inorganic nutrients were added. The materials were mixed as in example 1. Nitrogen was used to purge resident air. The daily results are set forth in the table below.

| | |
|---|---|
| 4 kg | ammonium phosphate |
| 100 g | wheat straw |
| 1 kg | Anaerobic soil (site rrs 12) |
| 2 kg | water |
| pH 7.5 | |

Nitrogen was fed into the fermentation vessel to purge any remaining air.

Results: (Example 2)
Recovery of Phosphite and Hypophosphite (% w/w as a % of the total P)

| | Day 1 | 3 | 6 | 9 | 12 | 15 | 18 | 21 | 24 |
|---|---|---|---|---|---|---|---|---|---|
| PO3/HPO2 | 0 | 0 | 8 | 10 | 10 | 11 | 10 | 9 | 8 |

EXAMPLE 3

Same as example 2, except that rock phosphate was used instead of ammonium phosphate.

| | |
|---|---|
| Rock phosphate | 4 Kg |
| Anaerobic soil (site rrs19) | 0.5 Kg |
| Wheat Straw | 0.5 Kg |
| Water | 4 Kg |

Results: (Example 3)
Recovery of Phosphite and Hypophosphite (% w/w as a % of the total P)

| | Day 1 | 3 | 6 | 9 | 12 | 15 | 18 | 21 | 24 |
|---|---|---|---|---|---|---|---|---|---|
| PO3/HPO2 | 0 | 0 | 5 | 6 | 12 | 11 | 5 | 7 | 3 |

EXAMPLE 4

In this example, all the components were sterilized. Then, a *Clostridium* species (C-rrs19) was added to the mixture after autoclaving and incubated as above.

| | |
|---|---|
| Ground (<0.25 mm) Rock phosphate | 4 Kg |
| Anaerobic soil (site rrs19) | 0.5 Kg |
| Wheat Straw | 0.5 Kg |
| Water | 4 Kg |

Results: (Example 4)
Recovery of Phosphite and Hypophosphite (% w/w as a % of the total P)

| | Day 1 | 3 | 6 | 9 | 12 | 15 | 18 | 21 | 24 |
|---|---|---|---|---|---|---|---|---|---|
| PO3/HPO2 | 0 | 0 | 0 | 0 | 6 | 16 | 12 | 3 | 3 |

EXAMPLE 5

In this example, as with example 4, all the components were sterilized. Then, an *E. coli* isolate (E.C. rrs 19) was added to the mixture after autoclaving and incubated as above.

| | |
|---|---|
| Rock phosphate | 4 Kg |
| Anaerobic soil (site rss19) | 0.5 Kg |
| Wheat Straw | 0.5 Kg |
| Water | 4 Kg |

Results: (Example 5)
Recovery of Phosphite and Hypophosphite (% w/w as a % of the total P)

| | Day 1 | 3 | 6 | 9 | 12 | 15 | 18 | 21 | 24 |
|---|---|---|---|---|---|---|---|---|---|
| PO3/HPO2 | 0 | 0 | 0 | 0 | 0 | 3 | 2 | 0 | 0 |

EXAMPLE 6

In this example, as with example 4, all the components were sterilized. Then, an unidentified bacterial isolate (UI rrs 19) was added to the mixture after autoclaving and incubated as above.

| | |
|---|---|
| Rock phosphate | 4 Kg |
| Anaerobic soil (site rss19) | 0.5 Kg |
| Wheat Straw | 0.5 Kg |
| Water | 4 Kg |

Results: (Example 6)
Recovery of Phosphite and Hypophosphite (% w/w as a % of the total P)

| | Day 1 | 3 | 6 | 9 | 12 | 15 | 18 | 21 | 24 |
|---|---|---|---|---|---|---|---|---|---|
| PO3/HPO2 | 0 | 0 | 3 | 10 | 16 | 18 | 17 | 18 | 16 |

What is claimed is:

1. A method for generating chemically reduced solid or liquid forms of phosphorus from a phosphorus source by anaerobic fermentation comprising the steps of:
   a. introducing a slurry containing a phosphate source into a vented chamber;
   b. introducing a source containing at least one microorganism into said chamber;
   c. introducing a carbon source into said chamber;
   d. introducing water into said chamber;
   e. incubating said chamber for a time period; and
   h. periodically removing said chemically reduced solid or liquid forms of phosphorus from said chamber.

2. The method of claim 1 wherein said incubation period is between a few days and a few months.

3. The method of claim 1 wherein the temperature in said chamber is maintained between about 10° C. and about 40° C.

4. The method of claim 1 wherein said microorganism source is soil.

5. The method of claim 1 wherein said microorganism source is naturally occurring soil.

6. The method of claim 1 wherein said microorganism source is naturally occurring microorganisms.

7. The method of claim 1 wherein said microorganism source is anaerobically cultivated soil.

8. The method of claim 7 wherein said soil contains anaerobic microbes and essential nutrients.

9. The method of claim 1 wherein anaerobic fungi is used in the fermentation process.

10. The method of claim 1 wherein anaerobic bacteria is used in the fermentation process.

11. The method of claim 1 wherein said phosphate source is selected from the group consisting of organic phosphate and inorganic phosphate.

12. The method of claim 1 wherein said phosphate source is a member selected from the group consisting of calcium phosphate, ammonium phosphate, potassium phosphate, rock phosphate, and combinations thereof.

13. The method of claim 1 wherein said organic phosphate source is a member selected from the group consisting of: animal sources, bones, plant sources, seeds, and combinations thereof.

14. The method of claim 1 wherein said chemically reduced forms of phosphorus are members selected from the group consisting of phosphite, hypophosphite, phosphonate, hypophosphonate, phosphonites, and combinations thereof.

15. The method of claim 1 comprising the further step of adding a neutralizing agent to maintain an effective pH for producing phosphites.

16. The method of claim 1 comprising the further step of maintaining the pH of the material in said chamber above about 4.8.

17. The method of claim 1 wherein said microorganism source is a bacteria selected from the group consisting of *Clostridium* genera, *Vibrio* genera, *Klebsiella, Escherichia* genera, and combinations thereof.

18. The method of claim 1 comprising the additional step of periodically venting said chamber.

19. The method of claim 1 comprising the additional step of purging air from said chamber prior to commencing fermentation.

20. The method of claim 19 wherein the step of purging is accomplished by introducing into the chamber a member selected from the group consisting of helium, nitrogen, a Noble gas, and combinations thereof.

21. The method of claim 1 comprising the additional step of purging excess air from said chamber by replacing it with at least one inert gas.

22. The method of claim 1 comprising the additional step of sterilizing said slurry before introducing said microorganism source.

23. The method of claim 22 wherein said microorganism source is a pure culture of selected microbes.

24. The method of claim 1 comprising the additional step of grinding up the fermentation components before introducing them into said chamber.

25. The method of claim 1 comprising the additional step of adjusting the initial pH of the material in said chamber to about 7.5.

26. The method of claim 1 wherein the reduced forms of phosphorus are used to formulate one of the group consisting of: agrochemicals, fertilizers, biocides, and combinations thereof.

27. The method of claim 1 wherein the reduced forms of phosphorus are applied to one of the group consisting of: plants, micro-organisms, the soil, and combinations thereof.

28. A method of converting higher oxidation state phosphorus molecules to lower oxidation state phosphorus molecules in solid or liquid by anaerobic fermentation comprising the steps of:
   a. introducing a slurry containing a source of phosphorus molecules in a higher oxidation state into a vented chamber;
   b. introducing a source containing at least one microorganism into said chamber;
   c. introducing a carbon source into said chamber;
   d. introducing water into said chamber;
   e. purging excess air from said chamber by replacing it with at least one inert gas;
   f. adjusting the initial pH of the material in said chamber to about 7.5;
   g. incubating said chamber to a temperature of between about 10° C. and about 40° C.;
   h. maintaining said temperature for a time period;
   i. maintaining the pH in said chamber above about 4.8; and
   j. periodically removing said lower oxidation state phosphorus molecules in solid or liquid form from said chamber.

29. The method of claim 28 wherein the source of said higher oxidation state phosphorus molecules is selected from the group consisting of: phosphate, naturally occurring phosphorus sources, synthetic phosphorus sources and combinations thereof.

30. The method of claim 28 wherein the source of said higher oxidation state phosphorus molecules is selected from the group consisting of organic phosphate and inorganic phosphate.

31. The method of claim 28 wherein the source of said higher oxidation state phosphorus molecules is a member selected from the group consisting of calcium phosphate, ammonium phosphate, potassium phosphate, sodium phosphate, magnesium phosphate, rock phosphate, and combinations thereof.

32. The method of claim 28 wherein said microorganism source is anaerobically cultivated soil.

33. The method of claim 28 wherein said microorganism source is a bacteria selected from the group consisting of *Clostridium* genera, *Vibrio* genera, *Klebsiella, Escherichia* genera, and combinations thereof.

34. The method of claim 28 comprising the additional step of sterilizing said slurry before introducing said microorganism source.

35. The method of claim 28 wherein the source of said higher oxidation state phosphorus molecules is a member selected from the group consisting of calcium phosphate, ammonium phosphate, potassium phosphate, magnesium phosphate, rock phosphate, and combinations thereof.

* * * * *